(12) United States Patent
Ito

(10) Patent No.: US 6,825,321 B1
(45) Date of Patent: Nov. 30, 2004

(54) PYREXIA-ASSOCIATED GENES AND PYREXIA-ASSOCIATED PROTEINS OF PLANTS

(75) Inventor: Kikukatsu Ito, Iwate (JP)

(73) Assignee: Japan Science and Technology Corporation, Saitama (JP)

( * ) Notice: Subject to any disclaimer, the term of this patent is extended or adjusted under 35 U.S.C. 154(b) by 299 days.

(21) Appl. No.: 10/009,962

(22) PCT Filed: Jun. 12, 2000

(86) PCT No.: PCT/JP00/03806

§ 371 (c)(1),
(2), (4) Date: Jan. 23, 2002

(87) PCT Pub. No.: WO00/77211

PCT Pub. Date: Dec. 21, 2000

(30) Foreign Application Priority Data

Jun. 14, 1999 (JP) .......................................... 11-167439

(51) Int. Cl.[7] .......................................... C07K 14/415
(52) U.S. Cl. ..................................................... 530/350
(58) Field of Search ......................................... 530/350

(56) References Cited

U.S. PATENT DOCUMENTS 6,602,694 B1 * 8/2003 Albrandt et al. ............ 435/183

FOREIGN PATENT DOCUMENTS

WO        WO 9632483     * 10/1996

OTHER PUBLICATIONS

Ito, K., "Isolation of two distinct cold–inducible cDNAs encoding plant uncoupling proteins from the spadix of skunk cabbage (Symplocarpus foetidus)", Plant Science, Dec. 1999, vol. 149, No. 2, pp. 167–173.

Ito, K. "A cold–inducible gene encoding uncoupling protein in thermogenic plant species" Cryobiology and Cryotechnology, Dec. 1999, vol. 45, No. 2, pp. 43–46.

Ricquier, D. et al., "The uncoupling protein homologues: UCP1, UCP2, UCP3, StUCP and AtUCP", Biochem. J., 2000, vol. 345, No. 2, pp. 161–179.

Watanabe, A. et al., "AtUCP2: a novel isoform of the mitochondrial uncoupling protein of Arabidopsis thaliana" Plant Cell Physiol., Nov. 1999, vol. 40, No. 11, pp. 1160–1166.

Maia I.G. et al., "AtPUMP: an Arabidopsis gene encoding a plant uncoupling mitochondrial protein", FEBS Letter, 1998, vol. 429, pp. 403–406.

Laloi, M. et al., "A plant cold–induced uncoupling protein", Nature, 1997, vol. 389, pp. 135–136.

* cited by examiner

Primary Examiner—Robert A. Wax
(74) Attorney, Agent, or Firm—Wenderoth, Lind & Ponack, L.L.P.

(57) ABSTRACT

The inventions of this application include thermogenic genes named SfUCPa and SfUCPb which are derived from skunk cabbage. cDNA of each gene comprises the base sequence of SEQ ID NO: 1 and 3, respectively. Thermogenic proteins, SfUCPA and SfUCPB, are expressed from genes SfUCPa and SfUCPb, sequence of SEQ ID NO: 2 and 4.

2 Claims, 10 Drawing Sheets

Fig. 3 Top

I

```
SfUCPA       1  ---MGDHGPRTEISFAGSSR--AAFAACFAELCTIPLDTAKVRLQLQKKAVTGDV-VALPKY   56
SfUCPB       1  ---MGDHGPRTEISFAGSSR--AAFAACFAELCTIPLDTAKVRLQLQKKAVTGDV-VALPKY   56
StUCP        1  MGGGDHGGKSDISFAGIFASSAFAACFAEACTIPLDTAKVRLQLQKRAVEGCG-LALPKY    59
AtPUMP       1  ---MVAAGKSDLSLPKTFACSAFAACVGEVCTIPLDTAKVRLQLQKSAFTLAGDVTLPKY    57
human UCP1   1  -MGGLTASDVHPTLGVQLFSAPIAACLADVITHPLDTAKVRLQVQGECP----TSSVIRY   55
human UCP2   1  -MVGFKATDVPPTATVKFLGAGTAACIADLITHPLDTAKVRLQIQGESQGPVRATASAQY   59
human UCP3   1  -MVGLKPSOVPPTMAVKFLGAGTAACFADLVTHPLDTAKVRLQIQGENQ-AVQTARLVQY   58
```

II

```
SfUCPA      57  RGMLGTVATIAREEGLSALWKGIVPGLHRQCLFGGLRIGLYEPVKSFYVG--DNFVGDIP  114
SfUCPB      57  RGMLGTVATIAREEGLSALWKGIVPGLHRQCLFGGLRIGLYEPVKSFYVG--DNFVGDIP  114
StUCP       60  RGLLGTVGTIAKEEGLASLWKGIVPGLHRQCIYGGLRIGHYEPVKNLYVG--KDHVGDVP  117
AtPUMP      58  RGLLGTVGTIAREEGLRSLWKGVVPGLHRQCLFGGLRIGMYEPVKNLYVFTGKDFVGDVP  117
human UCP1  56  KGVLGTITAVVKTEGRMKLYSGLPAGIAGLQRQISSASLRIGLYDTVQEFLTA--GKETAPS  112
human UCP2  60  RGVMGTILTMVRTEGPRSLYNGLVAGLQRQMSFASVRICLYDSVKQFYT---KGSEHAS  115
human UCP3  59  RGVLGTILTMVRTEGPCSPYNGLVAGLQRQMSFASIRIGLYDSVKQVYTP---KGADNSS  115
```

Fig. 3 Middle

```
                    III
sfUCPA    115  LSKKILAGLITGALAIVANPTDLVKVRLQSEGKLPPG--VPRRYSGALNAY--STIVKKE  171
sfUCPB    115  LSKKILAGLITGALAIVANPTDLVKVRLQSEGKLPPG--VPRRYSGALNAY--STIVKKE  171
stUCP     118  LSKKILAALTGALGITIANPTDLVKVRLQAEGKLPAG--VPRRYSGALNAY--STIVKQE  174
AtPUMP    118  LSKKILAGLITGALGIMVANPTDLVKVRLQAEGKLAAG--APRRYSGALNAYFTSTIVRQE  176
human UCP1 113 LGSKILAGLITGGVAVFIGQPTEVVKVRLQAQSHLHG--IKPRYTGTYNAY--RIIATTE  168
human UCP2 116 IGSRLLAGSTTGALAVAVAQPTDVVKVRFRAQARAG---GGRRYQSTVNAY--KTIAREE  170
human UCP3 116 LITRILAGCTTGAMAVTCAQPTDVVKVRFQASIHLGPSRSDRKYSGTMDAY--RTIAREE  173
                 *  ***   **    * ** **   *     *          *  *           +

IV                                              V
sfUCPA    172  GLGALWTGLGPNTARNAIINAAELASYDQVKQTILKLPGFSDNIFTHILAG--LGAGFFA  229
sfUCPB    172  GLGALWTGLGPNTARNAIINAAELASYDQVKQ----------------------------  203
stUCP     175  GVRALWTGLGPNIGRNAIINAAELASYDQVKEAVLRIPGFTDNVVTHLIAG--LGAGFFA  232
AtPUMP    177  GVRALWTVLGPNVARNAIINAAELASYDQVKETILKIPGFTDNVVTHILSGLFTGAGFFA  236
human UCP1 169 GLTGLWKGTTPNLMRSVIINCTELVTYDLMKEAFVKNNILADDVPCRLVSA--LIAGFCA  226
human UCP2 171 GFRGLWKGTSPNVARNAIVNCAELVTYDLIKDALLKANLMTDDLPCHFTSA--FGAGFCT  228
human UCP3 174 GVRGLWKGTLPNIMRNAIVNCAEVVTYDILKERLLDYHLLTDNFPCBFVSA--FGAGFCA  231
                  ***   **  * *   *  * * **  *                      *****
```

Fig. 3 Down

```
sfUCPA    230  VCIGSPVDVMKSRNMGDS--AYKSTFDCFIKILKNDGLLAFYRGFIPNFGRLG--SWNVI  285
sfUCPB    204  -----MKSRNMGDS--AYKSTFDCFIKILKNDGPLAFYRGFIPNFGRLG--SWNVI  250
stUCP     233  VCIGSPVDVVKSRNMGDS--AYKNTLDCFVKTLKNDGPLAFYRGFIPNFGRLG--SWNVI  288
AtPUMP    237  VCIGSPVDVVKSRNMGDSG-AYKGTIDCFVKTLKSDGPHAFYRGFIPNFGRLGSFTWNVI  295
human UCP1 227 TAMSSPVDVVKTRFINSPPGQYKSVPNCAMKVFTNEGPTAFFKGLVPSFLRLG--SWNVI  284
human UCP2 229 TVLASPVDVVKTRHMNSALGQYSSAGHCALTMLQKEGPRAFYKGFMPSFLRLG--SWNVV  286
human UCP3 232 TVVASPVDVVKTRHMNSPPGQYFSZLDCMIKMVAQEGPTAFYKGFTPSFLRLG--SWNVV  289
                    PNBD                                              VI sfUCPA    286  MFLTLEQVRKFFIKEVPN------  303
sfUCPB    251  MFLTLEQVRKFFIKEVPN------  268
stUCP     289  MFLTLEQAKKFVKSLESP------  306
AtPUMP    296  MFLTLEQAKKYVRELDASKRN--  316
human UCP1 285 MFVCFEQLKRELSKSRQTMDCAT  307
human UCP2 289 MFVTYEQLKRALMAACTSREAPF  309
human UCP3 290 MFVTIEQLKRALMKVQMLRESPF  312
```

PYREXIA-ASSOCIATED GENES AND PYREXIA-ASSOCIATED PROTEINS OF PLANTS

BACKGROUND OF THE INVENTION

1. Field of the Invention

The present invention relates to plant thermogenic genes and proteins. More particularly, the invention relates to thermogenic genes derived from a skunk cabbage (*Symplocarpus foetidus*) and gene products (proteins). Those genes and proteins are useful in breeding of cold-avoidance plants, medical treatment of diabetes metllitus or obesity, or development of novel thermogenic bio-materials.

2. Description of the Related Art

Stresses due to low temperatures, droughts and salinity are common harmful environmental factors that terrestrial plants encounter. Among these stresses, it has been considered that cellular injury due to the low temperature is the most important factor which restricts productivity of crops (Levitt, 1980). To resist the low temperature stress, cold-hardy plants such as wheat or rye have a variety of physiological and metabolic responses which lead to cold acclimation (Sakai and Larcher, 1987; Steponkus, 1984; Thomashow, 1998; Uemura and Steponkus, 1997). In contrast, it is known that some plants including skunk cabbage have a specialized system by which the plants generate heat to avoid freezing (Knutson, 1974; Nagy et al., 1972; Schneider and Buchenen, 1980).

The temperature of the flower in the spadix of skunk cabbage, which flowers in early spring, has been known to maintain its temperature at higher than +10° C. even when the ambient temperature falls to −15° C. (Knutson, 1974). For example, thermoscopic analysis using infrared camera indicates homeothermic behavior of the surface temperature of the spadix (FIG. 1). It should be noted that, in this experiment, the plants were placed in the growth chamber and the air temperature was gradually decreased. As clearly seen from FIG. 1, the temperature of the spadix of skunk cabbage is kept at approximately 19° C. notwithstanding a fall of the ambient temperature.

The temperature is thus maintained by doubling the respiration rate from the level of 12° C. to that of sub-zero temperature. It has also been considered that the heat production in thermogenic plant species relates to a cellular metabolism called cyanide-non-sensitive/non-phosphorylating electron-transferring pathway, which is controlled by mitochondrial alternative oxidase (AOX) (Berthold and Siedow, 1993, Ito et al., 1997; McIntosh, 1994, Wangner and Krab, 1995).

On the other hand, it has been shown that a mitochondrial protein called an uncoupling protein (UCP) plays an important role in generation of heat in mammals. UCP found in the intima of mitochondria make $H^+$ flow into the membrane to uncouple aspiration from synthesis of ATP which acts to disperse chemical energy to metabolic heat (Klaus et al., 1991; Kihngeberg and Winkler, 1985; Ricquier et al., 1991). In animals, 3 types of UCPs have been found. UCP1 is primarily distributed in brown adipose tissue (Nichollus and Locke, 1984). UCP2 is found ubiquitously in many tissues (Fleury et al., 1997), and UCP3 is localized specifically in skeletal muscle (Boss et al., 1997).

It has been considered that UCPs of mammals, similarly to other carrier proteins of mitochondria, are composed of 6 transmembrane segments, of which the hydrophobic portion is derived from pairing amphipathic α-helix structure (Liu et al., 1988; Maia et al., 1998). It is also known that the activity of these UCPs decreases depending on purine nucleotides (ATP, GTP, GDP and ADP) attached to the C-terminal legion and increases by free fatty acids (Jezek et al., 1998; Lin and Klingenberg, 1982; Katiyar and Shrago, 1989; Rial et al., 1983; Sluse et al., 1998).

On the contrary, 2 cDNAs encoding UCP-like proteins of plant origin were isolated from potato (StUCP: Laloi et al., 1997) and from Arabidopsis (AtPUMP: Maia et al., 1998). Since the expression of StUCP was mainly detected in the flower and the Suit, it has been postulated that StUCP may concern respiration during flowering and maturation of the fruit together with the AOX activity (Laloi et al., 1997).

Potato and Arabidopsis have been considered to be non-thermogenic plants. However, the expression of StUCP and AtPUMP have been induced by low temperature. Therefore, it has been suggested that these genes are involved in heat production (Laloi et al., 1997; Maia et al., 1998).

In the thermogenic plants such as skunk cabbage, however, UCP-mediated thermoigenic mechanisms have not yet been identified.

The purpose of the invention of this application is to provide unidentified novel UCP genes derived from a thermogenic plant, skunk cabbage.

The additional purpose of this application is to provide skunk cabbage UCPs which are expression products of the novel genes.

SUMMARY OF THE INVENTION

The invention provides thermogenic genes derived from skunk cabbage, i.e., gene SfUCPa of which cDNA comprises the base sequence of SEQ ID NO: 1, and gene SfUCPb of which cDNA comprises the base sequence of SEQ ID NO: 3.

Moreover, the invention provides thermogenic proteins, i.e., protein SfUCPA expressed from SfUCPa, which comprises the amino acid sequence of SEQ ID NO: 2, and protein SfUCPB expressed from SfUCPb, which comprises the amino acid sequence of SEQ ID NO: 4.

In addition, the invention provides cDNA having the base sequence of SEQ ID NO: 1 or a partial sequence thereof, and cDNA having the base sequence of SEQ ID NO: 3 or a partial sequence thereof.

BRIEF DESCRIPTION OF DRAWINGS

FIG. 3 compares the alignment of amino acid sequences of SfUCPA (SEQ ID No. 2) and SfUCPB (SEQ ID No. 4), together with potato UCP (StUCP) (SEQ ID No. 5), Arabidopsis UCP (AtPUMP) (SEQ ID No. 6) and human UCP (human UCP 1, 2 and 3 corresponding to SEQ ID Nos. 7, 8 and 9, respectively). The asterisks (*) attached under the sequences indicate the same amino acid sequence, and the dot (.) indicates the conservative change in all of the sequences. The boldface indicates the same sequence between SfUCPA (SEQ ID No. 2) and SfUCPB (SEQ ID No. 4). The gap introduced to optimize the sequence alignment is indicated by a dash (-). The alignment was made using a CLUSTAL W program. The characteristic domains of energy transfer proteins typical of mitochondria are surrounded by a square. The shaded bars (I~VI) above the upper sequence show estimated transmembrane domains.

DESCRIPTION OF THE PREFERRED EMBODIMENTS

In the gene SfUCPa of the present invention, its cDNA has the base sequence of SEQ ID NO: 1 and encodes the protein SfUCPA having the amino acid sequence of SEQ ID NO: 2, of which the estimated molecular weight is 32.6 kDa. In the gene SfUCPb of the present invention, its cDNA (SEQ ID NO: 3) encodes the protein SfUCPB having the amino acid sequence of SEQ ID NO: 4, of which the estimated molecular weight is 29.0 kDa.

Figure 1:
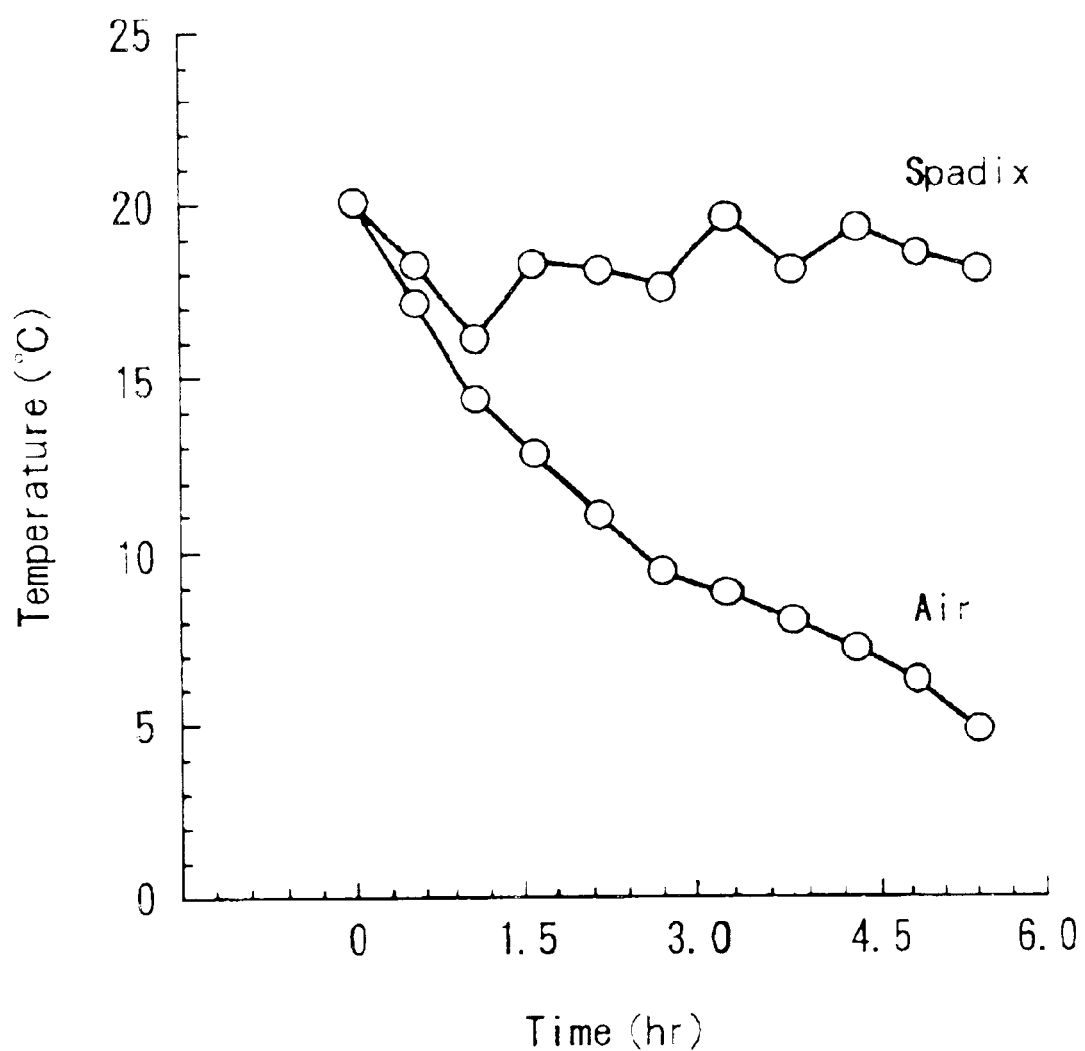
FIG. 1 shows the change of the temperature of the spadix in skunk cabbage and that of ambient temperature with a lapse of time.
Figure 2:
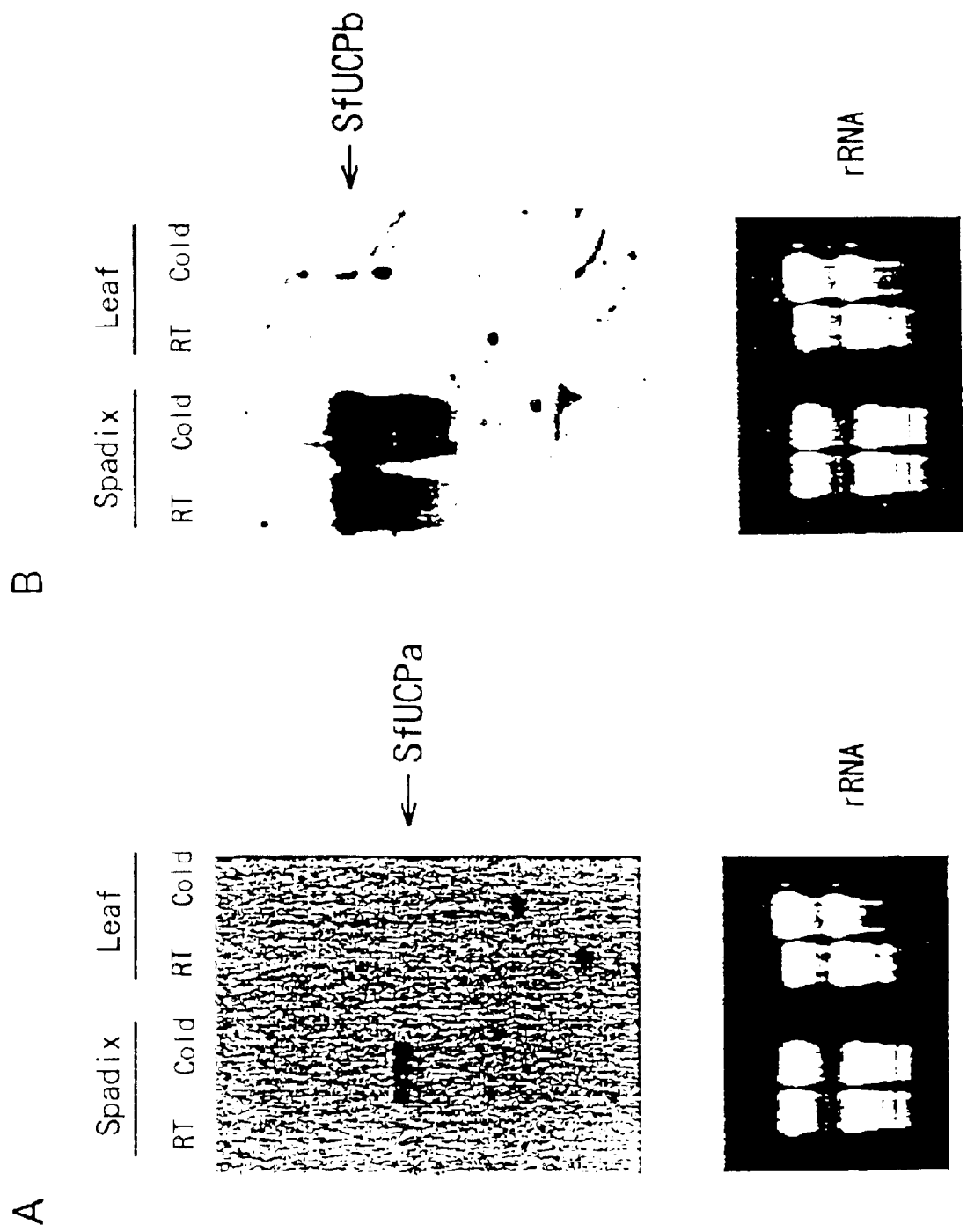
FIG. 2 shows the results of northern blottng, indicating the expression profile of SfUCPa (A) and SfUCPb (B) in the spadix and leaf of skunk cabbage at room temperature (RT) and during cold treatment (4° C. for 3 days). The lower figures respectively show the results of ethidium bromide staining of non-decomposed rRNA.

Genes SfUCPa and SfUCPb of the invention are derived from skunk cabbage, which are expressed specifically in the spadix when the temperature is low. The results of Northern blotting on the total RNAs extracted from skunk cabbage (Ito et al., 1999), confirmed that the expressions of both genes were detected in the spadices but not in the leaves at room temperature (15° C.) (FIG. 2). It was also confirmed that the spadix-specific expression of both genes were induced by cold treatment (4° C. for 3 days).

The amino acid sequences of the proteins SFUCPA and SFUCPB that are expressed from the respective genes of the invention have higher homology to the plant UCPs than to the human UCPs (FIG. 3) such that the amino acid sequence of SfUCPA has homology of 79%, 75%, 44%, 48% and 48% to StUCP, AtPUMP, human UCP, UCP2 and UCP3, respectively. SfUCPB has homology of 71%, 66%, 41%, 43% and 44%/o to StUCP, AtPUMP, human UCP, UCP2 and UCP3, respectively.

In addition, SfUCPA and SfUCPB have high sequence homology (88%) to each other though the region corresponding to the amino acid sequence between the 204th Thr and the 238th Val in SfUCPA is completely deleted in SfUCPB (FIG. 3). Moreover, the 265th Leu of SfUCPA is replaced by Pro in SfUCPB.

Figure 4:
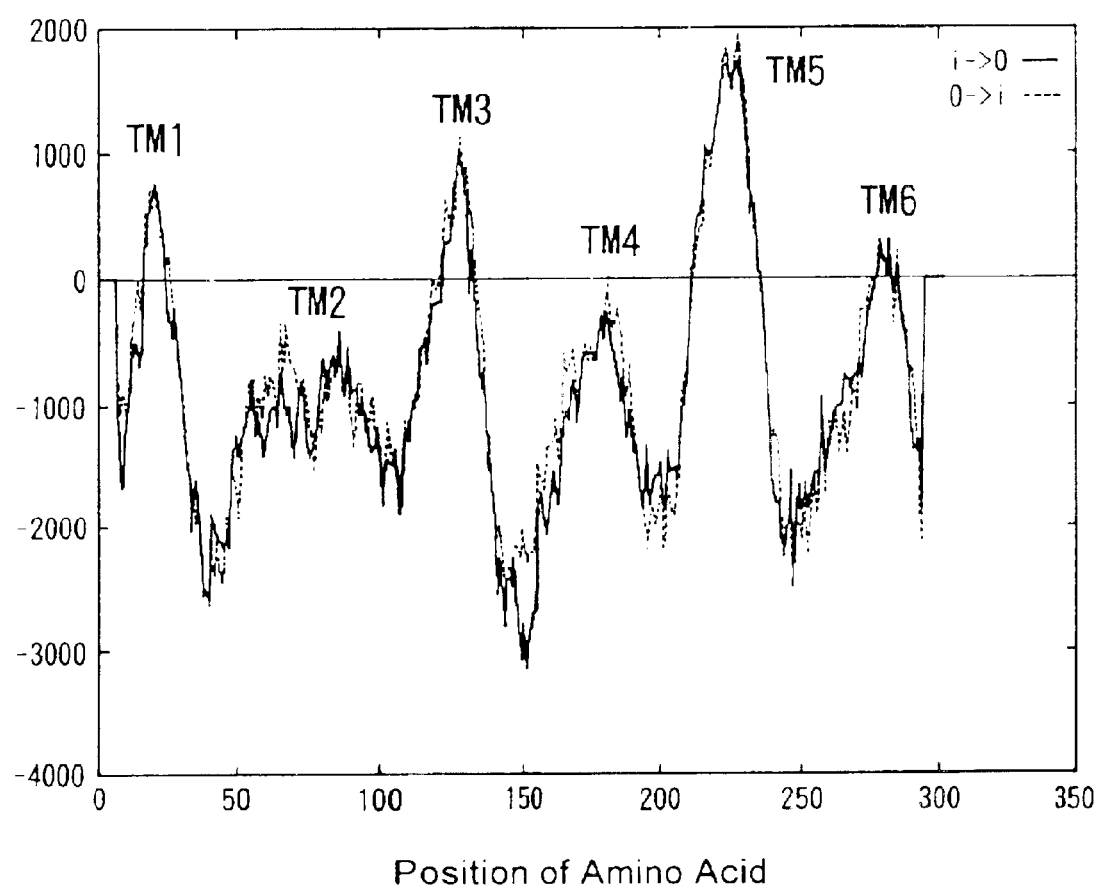
FIG. 4 shows a hydrophobic plot of SfUCPA. The vertical axis indicates the degree of hydrophobicity and the estimated transmembrane domains are indicated by TM1 to TM6.
Figure 5:
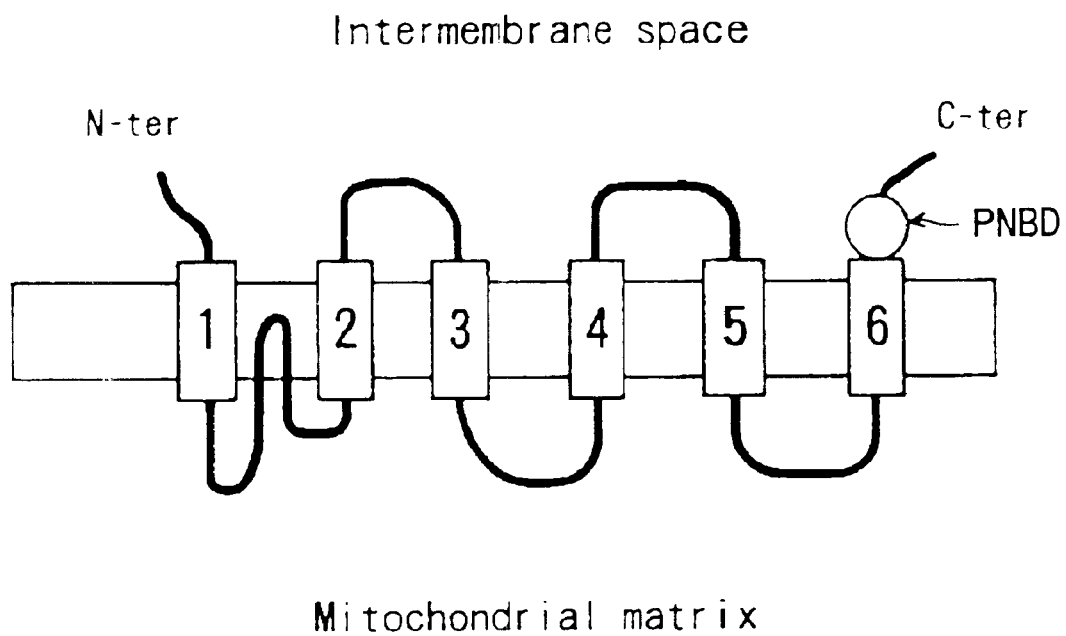
FIG. 5 shows a diagrammatic illustration of SfUCPA topology in the mitochondria membrane.
Figure 6:
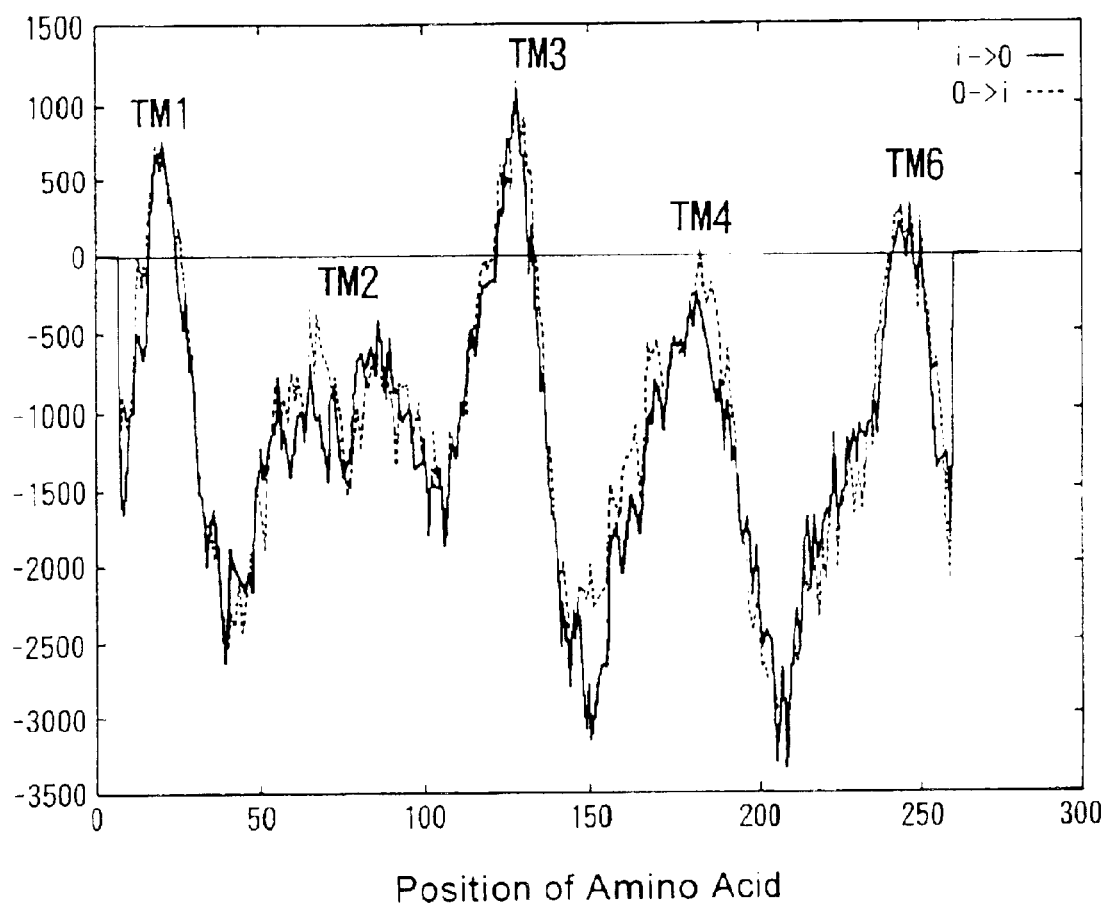
FIG. 6 shows a hydrophobic plot of SfUCPB. The vertical axis indicates the degree of hydrophobicity and the estimated transmembrane domains are indicated by TM1 to TM4 and TM6.
Figure 7:
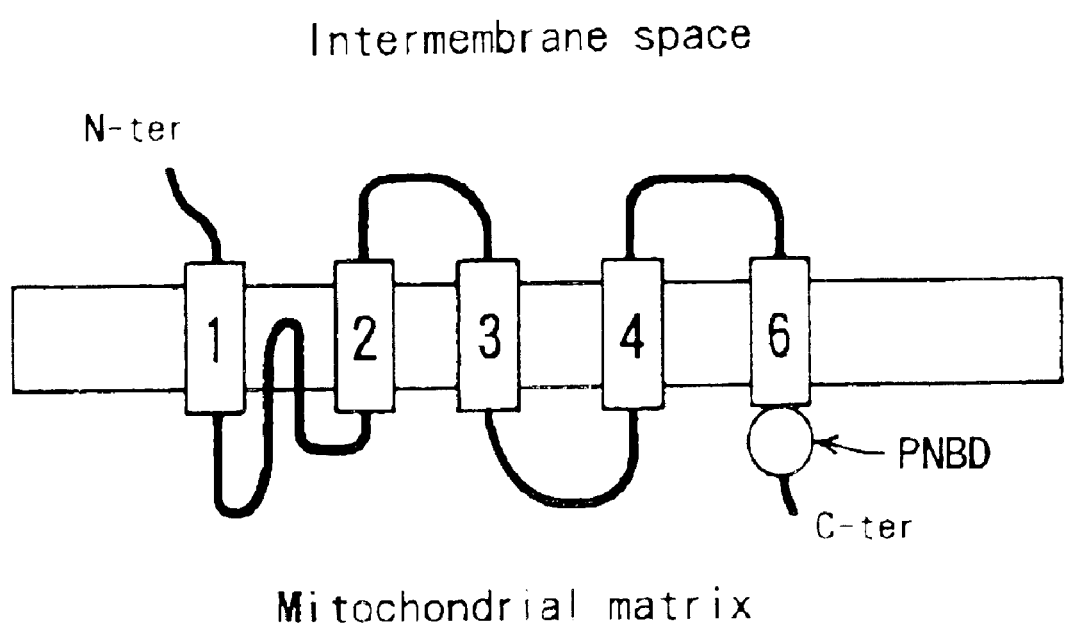
FIG. 7 shows a diagrammatic illustration of SfUCPB topology in the mitochondria membrane.

StUCPA has similar structure to that of other mitochondria UCP proteins. SfUCPA has 6 transmembrane domains as shown by the hydrophobic plot in FIG. 4, of which the topology is as shown in FIG. 5. In addition, this SfUCPA has 3 domains that are characteristic of energy transfer proteins in mitochondria (FIG. 3)(Boss et al., 1997; Maia et al., 1998). On the other hand, SfUCPB is lacking in the 3rd domain which is characteristic of energy transfer proteins in mitochondrial (FIG. 3), as well as in the 5th transmembrane domain (FIGS. 3 and 6). The topology is located toward the mitochondria matrix at the C-terminal (FIG. 7).

Each protein has a purine nucleotide-binding domain (PNBD) at the C-terminal (FIGS. 3, 5 and 7), and it is known that in UCP, binding of the purine nucleotide inhibits the uncoupling function in the mitochondria intima. In SfUCPB, however, there is a possibility that it may have escaped the inhibition of the binding of the purine nucleotide because its C-terminal is located toward the mitochondria matrix. Such a topology has not been found in any UCPs from animals or plants.

The thermogenic genes SfUCPa and SfUCPb provided by the invention are derived from skunk cabbage and are very useful in, for example, development of low temperature-tolerant plants using a genetic recombination technique. The proteins SfUCPA and SfUCPB that are expression products from the above genes are expected as effective components in remedies of diabetes mellitus, obesty, and the like, based on the uncoupling function to ATP synthesis. Moreover, such thermogenic proteins are also promising novel heat generating bio-materials.

The genes SfUCPa and SfUCPb of the invention can be isolated from the genomic DNA of skunk cabbage using the cDNA (SEQ ID NOS: 1 or 3) or a partial sequence thereof of the invention as a probe. For example, a genome library is prepared from the genomic DNA according to a known method. It may be screened by means of colony or plaque hybridization according to a mown method using as a probe an oligonucleotide synthesized based on the base sequence of an optional portion of cDNA. Alternatively, the target genetic region may also be identified by means of in situ hybridization for chromosome.

The respective cDNAs of the invention can be cloned, for example, from a cDNA library which is synthesized using a poly(A)*RNA of skunk cabbage as a template. In such a case, an oligonucleotide of an optional portion of cDNA provided by the invention is synthesized, which may be used as a probe to carry out screening by means of colony or plaque hybridization according to a known method. Alternatively, oligonucleotides which can hybridize to both ends of the target cDNA fragment are synthesized, which may be used as primers in preparation of cDNA of the invention by the RT-PCR method from mRNA isolated from the cells of skunk cabbage.

In general, polymorphism is frequently recognized in the genes of eucaryotic cells. In the invention, accordingly, in addition to cDNAs represented by SEQ ID NOS: 1 and 3, those in which one or several nucleotides are added, deleted and/or replaced by (an)other nucleotide(s) in the above cDNA are included. Similarly, proteins in which one or more amino acids are added, deleted and/or replaced by (an)other amino acid(s) due to change of the above nucleotide are also included in the present invention.

In cDNA of the invention, DNA fragments (10 bp or more) comprising an optimal part of the base sequences of SEQ ID NOS 1 and 3 are included. In addition, DNA fragments comprising a sense strand or anti-sense strand are also included.

The proteins of the invention, SfUCPA and SfUCPB, may be prepared respectively by a known method, for example, isolation from the spadix of skunk cabbage, preparation by chemical syntheses based on the amino acid sequence provided by the invention, or production by a recombinant DNA technique using cDNA provided by the invention. For example, when the protein is produced by a recombinant DNA technique, RNA is prepared from a vector containing cDNA of the invention by in vitro transcription, and this is used as a template for in vitro translation to yield the protein. Alternatively, the translational region of cDNA is incorporated into an appropriate expression vector according to a known method, and the resulting recombinant vector is introduced into *Escherichia coli, Baccillus subtilis*, yeast, animal or plant cells. The resulting transformants can be used in expression of the proteins in a large quantity.

In the case of the proteins of the invention being produced by in vitro translation, the translation region of cDNA of the invention may be incorporated into a vector containing RNA polymerase promotor, and then added to an in vitro translation system such as a rabbit reticulocyte lysate or wheat germ extract containing an RNA polymerase corresponding to the promotor. The RNA polymerase promotor is exemplified by T7, T3, SP6, and similar promoters.

In the case of the proteins of the invention being expressed in a microorganism such as *Eseherichia coli*, the translation region of cDNA is incorporated into an expression vector containing an origin replicable in microorganisms, promoter, ribosome binding site, cDNA cloning site, terminator, and the like, to construct a recombinant expression vector, which is then introduced into a host cell and incubated. In this operation, an initiation codon and a stop codon may be added to the front and tail of an optional translation region to obtain a protein fragment containing the optional region. Alternatively, the desired protein may be expressed as a fusion protein with another protein, which may be cleaved with a suitable protease to yield the desired protein. The expression vectors for *Escherichia coli* are exemplified by pUC series, pBluescript II, pET expression system, pGEX expression system, and the like.

In the case of the proteins of the invention being expressed in eucaryotic cells, the translation region of cDNA of the invention is incorporated into an expression vector for eucaryotic cells containing a promoter, splicing region, poly(A) additional site, and the like, and introduced into the eucaryotic cells. The expression vector is exemplified by pKA1, pCDM8, pSVK3, pMSG, pSVL, pBK-CMV, pBK-RSV, EVB-vector, pRS, pYES2, and the like. The eucaryotic cells, many include mammal cultured cells such as monkey renal cell COS7, Chinese hamster ovarian cell CHO, etc., budding yeast, fission yeast, silkworm cell, Xenopus egg cell, and the like are commonly used, but not limited thereto. In order to introduce the expression vector into eucaryotic cells, a known method such as electroporation, calcium phosphate method, liposane method, DEAE dextran method, and the like can be utilized.

After expression of the proteins in procaxyotic cells or eucaryotic cells according to the aforementioned method, the desired proteins are isolated and purified from the culture in the known combined procedures for separation. For example, treatment with a denaturant (e.g., urea) or surface activator, ultrasonication, digestion with enzymes, salting-out or solvent precipitation, dialysis, centrifugation, ultrafiltration, gel filtration, SDS-PAGE, isoelectric focusing, ion-exchange chromatography, hydrophobic chromatography, affinity chromatography, reverse phase chromatography, and the like are involved.

The proteins of the invention, SfUCPA and SfUCPB, also include peptide fragments (5 amino acids or more) involving the optional partial amino acid sequences of SEQ ID NOS: 2 and 4. In addition, the proteins of the invention also include fusion proteins with other optional proteins.

The following examples serve to illustrate the invention of this application specifically in more detail, but are not intended to limit the scope of the invention.

Example 1

Cloning of cDNA

The total RNA was extracted from the spadix of skunk cabbage (*Symplocarpus foetidus*) and the complete RNA was determined on 1.0% agarose gel electrophoresis (Ito et al., 1999). Using a mRNA isolation kit (Pharmacia), a clone associated with the UCP gene family was isolated from tie purified poly(A) $^+$RNA by RT-PCR. The first strand cDNA was prepared by annealing 20 pmol of cDNA primed primer (5'-TTTTTTTTTTTTTTTTTTTTTTTT-3') (SEQ ID No. 10) into poly(A) $^+$RNA (0.1 µg), followed by extension with 10 units of reverse transcriptase (New England Biolab) at 37° C. for 30 minutes in 20 µl of 1×RT buffer containing 10 mM 1,4 -dithiothreitol and 0.5 mM dNTP. The composition of the reaction solution is as follows.

10 mM Tris-HCl (pH 8.0);

50 mM KCl;

1.5 mM $MgCl_2$;

4 mM dNTP;

0.2 unit of EX Taq polymerase (Takara); and 10 pmol of two degenerate primers corresponding to the conserved amino acid sequence of the UCP family:

ZF1 (5'-CCIYTIGAYACIGCIAAR-3') (SEQ ID No. 11)

ZR1 (5'-ACWTTCCAISYICCIAWIC-3') (SEQ ID No. 12).

PCR cycle was carried out as follows.

(94° C.: 0.5 minute; 50° C.: 1 minute; 72° C.: 1 minute)× 35

Among the PCR products obtained in the above method, the amino acid sequence estimated from the sequence of about 0.8kb cDNA fragment had very high homology to one of the reading frame sequences of the UCP gene family. This fragment, accordingly, was cloned into T-vector (clone p2-1) and used as a probe for library screening.

cDNA (5µg) prepared from the spadix was inserted into λgt 11 phage according to the known method (Sambrook et al., 1989) to construct a cDNA library. From this library, 8 clones positive to the above-described probes were isolated and sub-cloned into the pBluescript SK plasmid (Stratagene). From these clones, clones pz8-1 and pz8-2 were obtained, which respectively contained the full length SfUCPa cDNA and SfUCPb cDNA.

The insert in each clone was sequenced with an auto-sequencer ABI373A using the BcaBest sequencing kit (Takara) and T3, T7 and gene-specific primers. The sequence data were analyzed by means of the GENEITYX-Homology Software System version 2.2.0 (Software Development).

cDNA of SfUCPa had the 1,525 bp base sequence of SEQ ID NO: 1, and cDNA of SfUCPb had the 2,991 bp base sequence of SEQ ID NO: 3 An estimated polyadenylated signal (aataaa) was found upstream of 236 bp from the poly(A) sequence in cDNA of SfUCPa, while in cDNA of SfUCPb two polyadenylated sites were recognized at the positions of 1,171 bp and 1,243 bp. It is noteworthy that cDNA of SfUCPb has a longer 3'-untranslation region than that of SfUCPa.

cDNA of SfUCPa had an open reading frame (ORF) encoding 303 amino acids as shown in SEQ ID NO: 1, and this ORF was found to encode the protein SfUCPA of the estimated molecular weight 32.6 kDa having the amino acid sequence of SEQ ID NO: 2. On the other hand, cDNA of SfUCPb had an ORF corresponding to 268 amino acids as shown in SEQ ID NO: 3, and found to encode the protein SfUCPB of the estimated molecular weight 29.0 kDa.

Moreover, it was confirmed from the results of Southern blot analysis that the genome of skunk cabbage contains multiple copies of SfUCPa gene and a single copy of SfUCPb (data not shown).

Example 2

In Vitro Translation of cDNA

The plasmid clones pz8-1 and pz8-2 obtained in Example 1 were linearized, on which a sense- or anti-sense RNA was transcribed with T7 RNA polymerase or T3 RNA polymerase according to the protocol of MAXICRIPT transcription kit (Ambion). An equal amount of RNA (4 μg) was provided for in vitro translation reaction using a wheat germ extract (Promega) in the presence of $^{35}$S-methionine (Amersham). The translation product was analyzed by SDS-PAGE. The gel was fixed, incubated in Amplify (Amersham), then dried, and fluorometrically analyzed.

Figure 8:
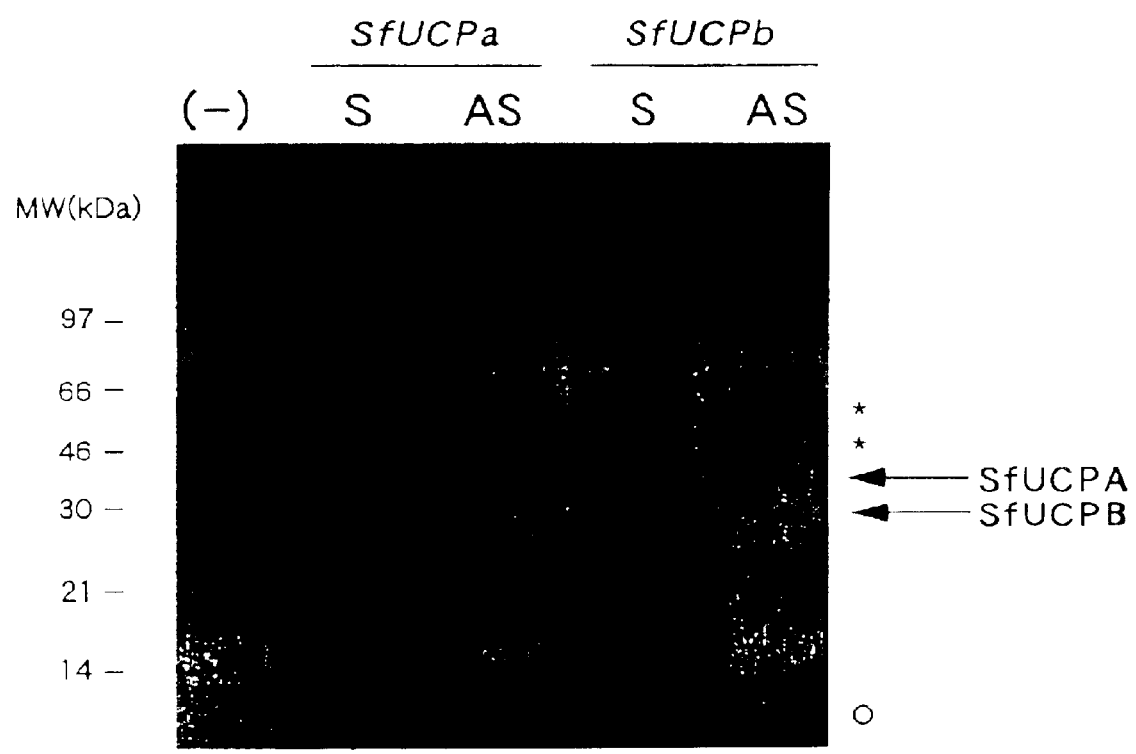
FIG. 8 shows the results of in vitro translation using respective cDNAs of the genes SfUCPa and SfUCPb as templates. (–) indicates a control, S a sense RNA, and AS an antisense RNA. The asterisk (*) indicates a non-specific product and the empty circle denotes the position of a low molecular translated artificial product synthesized from a small ORF.

As a result, it was confirmed that, as shown in FIG. 8, the initiation codon and the stop codon of cDNA isolated in Example 1 functioned successfully since a protein having an expected molecular weight was produced from any of cDNAs only when the sense RNA was used as a template.

As described previously, this application provides novel thermogenic genes SfUCPa and SfUCPb as well as their gene products, i.e., thermogenic proteins SfUCPA and SfUCPB, derived from skunk cabbage (*Symplocarpus foetidus*), and cDNAs used for gene engineering mass production of these proteins. These genes and proteins allow development of low temperature-tolerant plants, development of drugs or methods for treatment of diabetes mellitus or obesity, or development of novel heat generating materials from plants.

References

Berthold and Siedow (1993) Plant Physiol. 101, 113–119.
Boss et al. (1997) FEBS Lett. 408, 39–42.
Fleury et al. (1997) Nature Genetics 15, 269–272.
Ito, K. et al. (1999) Plant Sci. 142, 57–65.
Ito, K. et al. (1994) Nucl. Acids Res. 22, 2036–2041.
Ito, Y. et al. (1997) Gene 12, 121–129.
Jezek et al. (1998) Biochem. Biophys. Acta 1365, 319–327.
Katiyar and Shrago (1989) Nati. Acad. Sci. USA 86, 2559–2562.
Klaus et al. (1991) Int. J. Biochem. 23, 791–810.
Klingenberg and Winkler (1985) EMBO J. 4, 3087–3092.
Knutson (1974) Science 186, 746–747.
Laloi et al. (1997) Nature 389, 135–136.
Levitt (1980) Responses of plants to environmental stresses. 2nd edn. New York: Academic Press.
Lin and Klingenberg (1982) Biochemistry, 21, 2950–2956.
Liu et al. (1988) J. Cell. Biol. 107, 503–509.
Maia et al. (1998) FEBS Lett. 429, 403–406.
McIntosh (1994) Plant Physiol. 105, 781–786.
Nagy et al. (1972) Science 178, 1195–1197.
Nicholls and Locke (1984) Physiol. Rev. 64, 1–64.
Rial et al. (1983) Eur. J. Biochem. 137, 197–203.
Ricquier et al. (1991) FASEB J. 5,2237–2242.
Sakai and Larcher (1987) Frost Survival of Plants: Responses and Adaptations to Freezing Stresses. Berlin and New York; Springer-Verlag.
Sambrook et al. (1989) Molecular Cloning: A Laboratory Manual, 2nd eds. New York; Cold Spring Harbor Laboratory Press.
Schneider and Buchanan (1980) Amer. J. Bot. 67, 182–193.
Sluse et al. (1998) FEBS Lett. 433, 237–240.
Steponkus (1984) Annu Rev. Plant Physiol. 35, 543–581.
Thomashow (1998) Plant Physiol. 118, 1–7.
Uemura and Steponkus (1997) Plant Cold Hardiness: Molecular Biology, Biochemistry, and Physiology (Li and Chen, edn). New York: Plenum Press, pp. 171–179.
Physiol. Plant, 95, 318–325.

What is claimed is:

1. A thermogenic protein SfUCPA which comprises the amino acid sequence of SEQ ID NO: 2.

2. A Thermogenic protein SfUCPB which comprises the amino acid sequence of SEQ ID NO: 4.

* * * * *

SEQUENCE LISTING

```
<160> NUMBER OF SEQ ID NOS: 12

<210> SEQ ID NO 1
<211> LENGTH: 1525
<212> TYPE: DNA
<213> ORGANISM: Symplocarpus foetidus
<220> FEATURE:
<221> NAME/KEY: CDS
<222> LOCATION: (280)..(1188)
<220> FEATURE:
<221> NAME/KEY: poly A site
<222> LOCATION: (1271)..(1276)
<300> PUBLICATION INFORMATION:
<301> AUTHORS: Ito, K.
<302> TITLE: Isolation of two distinct cold-inducible cDNAs encoding
      plant uncoupling proteins from the spadix of skunk cabbage
      (Symplocarpus foetidus)
<303> JOURNAL: Plant Sci.
<304> VOLUME: 149
<305> ISSUE: 2
<306> PAGES: 167-173
<307> DATE: Dec-1999
<308> DATABASE ACCESSION NUMBER: GenBank AB024733
<309> DATABASE ENTRY DATE: 2000-02-25
```

-continued

```
<400> SEQUENCE: 1
gaggattcgc agaagaaagg ccagaacccg attccttccc gtcttcttct ccttccgccc      60
aattgcagtt tttcgcagcg gcgtcatcat caagaccctc cgcctttccg cgccaaacgc     120
cttccacccc cacccaatcg ccctccgttt cccgaaatat tcctcttccc tcctcccttt     180
tcttctctac ataaacccta accacccccat cctctcctcc cgcttccgac caccctgcat    240
tctactggga gcccatttga tcgaggtttc ccggcgagg atg ggc gat cac ggc         294
                                             Met Gly Asp His Gly
                                              1               5 ccg agg acc gag atc tcg ttt gcc ggc agt tcg cga gca gca ttc gcc       342
Pro Arg Thr Glu Ile Ser Phe Ala Gly Ser Ser Arg Ala Ala Phe Ala
              10                  15                  20 gct tgc ttc gcc gag ctt tgc acg att ccg ttg gac act gct aaa gtt       390
Ala Cys Phe Ala Glu Leu Cys Thr Ile Pro Leu Asp Thr Ala Lys Val
          25                  30                  35 agg ctt caa ctc caa aag aaa gca gta aca ggt gat gtg gtg gct ttg       438
Arg Leu Gln Leu Gln Lys Lys Ala Val Thr Gly Asp Val Val Ala Leu
      40                  45                  50 cca aaa tac agg gga atg ttg ggc act gtt gcc act att gcc agg gag       486
Pro Lys Tyr Arg Gly Met Leu Gly Thr Val Ala Thr Ile Ala Arg Glu
  55                  60                  65 gaa ggt ttg tcg gca ctc tgg aaa gga att gta ccc ggt ttg cat cgt       534
Glu Gly Leu Ser Ala Leu Trp Lys Gly Ile Val Pro Gly Leu His Arg
 70                  75                  80                  85 caa tgc ctc ttt gga ggg cta cga att ggg ttg tat gaa cca gtt aag       582
Gln Cys Leu Phe Gly Gly Leu Arg Ile Gly Leu Tyr Glu Pro Val Lys
              90                  95                 100 tcc ttt tat gtt gga gat aac ttt gtt gga gat att cct tta tcc aag       630
Ser Phe Tyr Val Gly Asp Asn Phe Val Gly Asp Ile Pro Leu Ser Lys
         105                 110                 115 aaa ata ctt gct ggg ctt aca aca ggt gca tta gca att ata gtg gca       678
Lys Ile Leu Ala Gly Leu Thr Thr Gly Ala Leu Ala Ile Ile Val Ala
     120                 125                 130 aat ccc act gac ctt gtt aaa gtt cga ctt caa tct gaa ggt aaa ctc       726
Asn Pro Thr Asp Leu Val Lys Val Arg Leu Gln Ser Glu Gly Lys Leu
 135                 140                 145 ccc cct ggg gta ccg aga cgt tat tca ggg gcg cta aat gct tat tca       774
Pro Pro Gly Val Pro Arg Arg Tyr Ser Gly Ala Leu Asn Ala Tyr Ser
150                 155                 160                 165 acc ata gtc aaa aag gaa gga ctt ggt gct ctg tgg act ggg ctt ggt       822
Thr Ile Val Lys Lys Glu Gly Leu Gly Ala Leu Trp Thr Gly Leu Gly
             170                 175                 180 cct aat att gcc cgc aat gct att ata aat gct gct gaa ttg gcc agt       870
Pro Asn Ile Ala Arg Asn Ala Ile Ile Asn Ala Ala Glu Leu Ala Ser
         185                 190                 195 tat gat caa gtg aaa cag aca atc tta aaa tta cca gga ttc tca gat       918
Tyr Asp Gln Val Lys Gln Thr Ile Leu Lys Leu Pro Gly Phe Ser Asp
     200                 205                 210 aat att ttt act cat att tta gcc ggt ctg ggg gca ggt ttt ttt gcc       966
Asn Ile Phe Thr His Ile Leu Ala Gly Leu Gly Ala Gly Phe Phe Ala
 215                 220                 225 gtc tgt atc ggt tct cct gtt gat gtg atg aag tct aga atg atg gga      1014
Val Cys Ile Gly Ser Pro Val Asp Val Met Lys Ser Arg Met Met Gly
230                 235                 240                 245 gat tca gcc tac aaa agc aca ttt gat tgt ttc atc aag aca ttg aaa      1062
Asp Ser Ala Tyr Lys Ser Thr Phe Asp Cys Phe Ile Lys Thr Leu Lys
             250                 255                 260 aat gat ggg ctt ctt gct ttt tac aag ggg ttt atc cca aac ttt ggt      1110
```

-continued

```
Asn Asp Gly Leu Leu Ala Phe Tyr Lys Gly Phe Ile Pro Asn Phe Gly
            265                 270                 275 cgg tta gga tcg tgg aat gtg atc atg ttt ttg acc ttg gag cag gtc    1158
Arg Leu Gly Ser Trp Asn Val Ile Met Phe Leu Thr Leu Glu Gln Val
            280                 285                 290 aag aag ttt ttc atc aaa gag gtg cca aat taatacattg aactcggata      1208
Lys Lys Phe Phe Ile Lys Glu Val Pro Asn
            295                 300 ggagtagaaa gaaagggttt tgtggaatt ttctctaccg gtgtggatcc tggcgagaga   1268
caaataaatc ttcctgactg ctcagatgtg tacctttttt atgaatggtt cttttcttat  1328
agaggacaga gaaaagaaaa aaaaaatcat tgtcatttac tcttttccc catttctgct   1388 gctaatcttg gtaggagaag aaaagtctta cattgagtga taacgttgtt ctctgcatcc  1448 attattttc agagatacta tttgacacat gaaaagtaat gcacatcagg ttttttttaa   1508
aaaaaaaaaa aaaaaaa                                                 1525
```

<210> SEQ ID NO 2
<211> LENGTH: 303
<212> TYPE: PRT
<213> ORGANISM: Symplocarpus foetidus

<400> SEQUENCE: 2

```
Met Gly Asp His Gly Pro Arg Thr Glu Ile Ser Phe Ala Gly Ser Ser
  1               5                  10                  15

Arg Ala Ala Phe Ala Ala Cys Phe Ala Glu Leu Cys Thr Ile Pro Leu
             20                  25                  30

Asp Thr Ala Lys Val Arg Leu Gln Leu Gln Lys Lys Ala Val Thr Gly
         35                  40                  45

Asp Val Val Ala Leu Pro Lys Tyr Arg Gly Met Leu Gly Thr Val Ala
     50                  55                  60

Thr Ile Ala Arg Glu Glu Gly Leu Ser Ala Leu Trp Lys Gly Ile Val
 65                  70                  75                  80

Pro Gly Leu His Arg Gln Cys Leu Phe Gly Gly Leu Arg Ile Gly Leu
                 85                  90                  95

Tyr Glu Pro Val Lys Ser Phe Tyr Val Gly Asp Asn Phe Val Gly Asp
            100                 105                 110

Ile Pro Leu Ser Lys Lys Ile Leu Ala Gly Leu Thr Thr Gly Ala Leu
            115                 120                 125

Ala Ile Ile Val Ala Asn Pro Thr Asp Leu Val Lys Val Arg Leu Gln
        130                 135                 140

Ser Glu Gly Lys Leu Pro Pro Gly Val Pro Arg Arg Tyr Ser Gly Ala
145                 150                 155                 160

Leu Asn Ala Tyr Ser Thr Ile Val Lys Lys Glu Gly Leu Gly Ala Leu
                165                 170                 175

Trp Thr Gly Leu Gly Pro Asn Ile Ala Arg Asn Ala Ile Ile Asn Ala
            180                 185                 190

Ala Glu Leu Ala Ser Tyr Asp Gln Val Lys Gln Thr Ile Leu Lys Leu
        195                 200                 205

Pro Gly Phe Ser Asp Asn Ile Phe Thr His Ile Leu Ala Gly Leu Gly
    210                 215                 220

Ala Gly Phe Phe Ala Val Cys Ile Gly Ser Pro Val Asp Val Met Lys
225                 230                 235                 240

Ser Arg Met Met Gly Asp Ser Ala Tyr Lys Ser Thr Phe Asp Cys Phe
                245                 250                 255
```

-continued

```
Ile Lys Thr Leu Lys Asn Asp Gly Leu Leu Ala Phe Tyr Lys Gly Phe
            260                 265                 270

Ile Pro Asn Phe Gly Arg Leu Gly Ser Trp Asn Val Ile Met Phe Leu
        275                 280                 285

Thr Leu Glu Gln Val Lys Lys Phe Phe Ile Lys Glu Val Pro Asn
    290                 295                 300
```

<210> SEQ ID NO 3
<211> LENGTH: 2991
<212> TYPE: DNA
<213> ORGANISM: Symplocarpus foetidus
<220> FEATURE:
<221> NAME/KEY: CDS
<222> LOCATION: (286)..(1089)
<220> FEATURE:
<221> NAME/KEY: poly A site
<222> LOCATION: (1171)..(1176)
<220> FEATURE:
<221> NAME/KEY: poly A site
<222> LOCATION: (1243)..(1248)
<300> PUBLICATION INFORMATION:
<301> AUTHORS: Ito, K.
<302> TITLE: Isolation of two distinct cold-inducible cDNAs encoding
      plant uncoupling proteins from the spadix of skunk cabbage
      (Symplocarpus foetidus)
<303> JOURNAL: Plant Sci.
<304> VOLUME: 149
<305> ISSUE: 2
<306> PAGES: 167-173
<307> DATE: Dec-1999
<308> DATABASE ACCESSION NUMBER: GenBank AB024734
<309> DATABASE ENTRY DATE: 2000-02-25

<400> SEQUENCE: 3

```
tggtggtgac gagtgacgag gattcgcaga agaaaggcca gaacccgatt ccttcccgtc    60
ttcttctcct tccgcccaat tgcagttttt cgcagcgggt catcatcaag accctccgcc   120
tttccgcgcc aaacgccttc cacccaatcc ctccgtttcc cgaaatattc cccttccctc   180 cctttcttc tctacataaa ccctaaccac ccccatcctc tcctcccgct tccgaccacc    240
ctgcattcta ctgggatccc atttgatcga cgtttcccgg cgagg atg ggc gat cac   297
                                              Met Gly Asp His
                                                1 ggc ccg agg acc gag atc tcg ttt gcc ggc agt tcg cga gca gca ttc    345
Gly Pro Arg Thr Glu Ile Ser Phe Ala Gly Ser Ser Arg Ala Ala Phe
  5               10                  15                  20 gcc gct tgc ttc gcc gag ctc tgt acg att ccg ttg gac act gct aaa    393
Ala Ala Cys Phe Ala Glu Leu Cys Thr Ile Pro Leu Asp Thr Ala Lys
             25                  30                  35 gtt agg ctt cag ctc caa aag aaa gca gta aca ggt gat gtg gtg gct    441
Val Arg Leu Gln Leu Gln Lys Lys Ala Val Thr Gly Asp Val Val Ala
         40                  45                  50 ttg cca aaa tac agg gga atg ttg ggc act gtt gcc act att gcc agg    489
Leu Pro Lys Tyr Arg Gly Met Leu Gly Thr Val Ala Thr Ile Ala Arg
     55                  60                  65 gag gaa ggt ttg tcg gca ctc tgg aaa gga att gta ccc ggt ttg cat    537
Glu Glu Gly Leu Ser Ala Leu Trp Lys Gly Ile Val Pro Gly Leu His
 70                  75                  80 cgt caa tgc ctc ttt gga ggg cta cga att ggg ttg tat gaa cca gtt    585
Arg Gln Cys Leu Phe Gly Gly Leu Arg Ile Gly Leu Tyr Glu Pro Val
 85                  90                  95                 100 aag tcc ttt tat gtt gga gat aac ttt gtt gga gat att cct tta tcc    633
Lys Ser Phe Tyr Val Gly Asp Asn Phe Val Gly Asp Ile Pro Leu Ser
                105                 110                 115 aag aaa ata ctt gct ggg ctt aca aca ggt gca tta gca att ata gtg    681
```

```
                Lys Lys Ile Leu Ala Gly Leu Thr Thr Gly Ala Leu Ala Ile Ile Val
                            120                 125                 130 gca aat ccg act gac ctt gtt aaa gtt cga ctt caa tct gaa ggt aaa       729
Ala Asn Pro Thr Asp Leu Val Lys Val Arg Leu Gln Ser Glu Gly Lys
            135                 140                 145 ctc ccc cct ggg gta cca aga cgt tat tca ggg gcg cta aat gct tat       777
Leu Pro Pro Gly Val Pro Arg Arg Tyr Ser Gly Ala Leu Asn Ala Tyr
        150                 155                 160 tca acc ata gtc aaa aag gaa gga ctt ggt gct ctg tgg act ggg ctt       825
Ser Thr Ile Val Lys Lys Glu Gly Leu Gly Ala Leu Trp Thr Gly Leu
165                 170                 175                 180 ggt cct aat att gcc cgc aat gct att ata aat gct gct gaa ttg gcc       873
Gly Pro Asn Ile Ala Arg Asn Ala Ile Ile Asn Ala Ala Glu Leu Ala
                185                 190                 195 agt tat gat caa gtg aaa cag atg aag tct aga atg atg gga gat tca       921
Ser Tyr Asp Gln Val Lys Gln Met Lys Ser Arg Met Met Gly Asp Ser
            200                 205                 210 gcc tac aaa agc aca ttt gat tgt ttc atc aag acg ttg aaa aat gat       969
Ala Tyr Lys Ser Thr Phe Asp Cys Phe Ile Lys Thr Leu Lys Asn Asp
        215                 220                 225 ggg cct ctt gct ttt tac aag ggg ttt atc cca aac ttt ggt cgg tta      1017
Gly Pro Leu Ala Phe Tyr Lys Gly Phe Ile Pro Asn Phe Gly Arg Leu
    230                 235                 240 gga tcg tgg aat gtg atc atg ttt ttg acc ttg gag cag gtc aag aag      1065
Gly Ser Trp Asn Val Ile Met Phe Leu Thr Leu Glu Gln Val Lys Lys
245                 250                 255                 260 ttc ttc atc aaa gag gtg cca aat taatacattg aagtcggata ggagtagaaa     1119
Phe Phe Ile Lys Glu Val Pro Asn
                265 aaaagggttt ttgtggaatt ttctctaccg gtgtggatcc tggcgagaga gaataaatct    1179 tcctgactgc tcagatgttg taccttttt atgaatggtt cttttcttat agaggacaga    1239 gaaaataaaa gaaaaattca ttgtcatgta ctcttttcc ccatttctgc tgagtagcag    1299 ctataccaag cagactttgt tgcttggctg ctgctaatct tgtagctgaa gaaaagtctt   1359 acattgagtg ataacgttgt tctctgcatc cattattttt cagagttact atttgacaca   1419 tgaaaagttt tttttttttt ttttttttt aacaggcagc aaatagagga atcgatctca    1479 cgactatcct ctttattcat taacaggcat acaaacttag ggagagcatg cagggtatat   1539 atcaaaatat acccttttat tagacatttt gcgtacacag ttggtcctca aacgactgta   1599 tctagcagcc aattttaga ccacattaag acagagagaa acaagcagaa gaacagggta    1659 ccatacatac ataggtaata attaagatga tgaacatagc ataggttcat gatctacttc   1719 ttcttcacgt acacatgatg caccagctga atgggaatct tggtcaccat atggcatgaa   1779 agtacgtcat gtgcagacgt tatatagtgt tcttcttacc attcagcagc agcaccagag   1839 gcatcaaaca ctggggtctt gacagggtat gaggggtaca ttgcgatccc acacatgccg   1899 tagggagtca cattgcgttt gatttttatg tatccagcct gtccccacct agtgccccat   1959 gagttcctta caagccaata atccttccca tcctccgaac catatcctat tatcaccaca   2019 gcatggtcga tacgttgacc acatggtcca gcaaatacgc ccgaggtgta gtgttggaat   2079 ccagcgcccg aagcctcaag agcaacactg acaggttgct ttgcgactgc atactgtagg   2139 ctaacctcgt tgtacggaga aacatttca tacgcatcaa tcgaggtgac tttaataaga    2199 tttgctctgc aagttcctcg acgtcctgtg tacgggtaat ttttgaaaaa aggagaaggg   2259 cgggaagaag cgcgcgtctc tgctcgcgac gggttaattc ttcatatggc cacttcgagc   2319
```

```
atggcttcgg cagcctccag cttcgttctc actccggcct ccctccacc accacgccgg    2379 ttcccccgtc cgccttcttt cccagggtcg caggaggctc gtggtggtgc gggccgagga    2439
agccgcgacg accccccgccc ccggcgccgg cggagggagc cgcgccgccg ccccaagcc    2499 gccaccgatc gggcccaaga gggggtcaaa ggttgatata tagttcttaa tttctttccc    2559
gtgtggcttc tggagttaga tttgtttcct cttctctttt tttgttttgt ttttcaatt    2619 taaattttat tctcatctgt ggacgacctt ccatcggggt tttcgtccct ctcgcaggtg    2679
aagatctccg gaaggaatcc tactggttca acggtgtcgg atcggtggtg gctgttgatc    2739
aggatccggc gactcgatac ccggtcgtgg ttcggttcac caaggtcaac tatgcgaacg    2799
tctcgaccaa caactacgca ctggacgaga tcctggaggt gaaatgaggg tcggcgggcg    2859
tggtcggtcg ggcatgtcac gatgatgtat tttcgcagtt ggtagtgtaa aataccatgt    2919
cattcgtgta aaactctttc gttcgccaaa tcctcagttg aaattttaat tcccagccag    2979
taaaaaaaaa aa                                                        2991
```

<210> SEQ ID NO 4
<211> LENGTH: 268
<212> TYPE: PRT
<213> ORGANISM: Symplocarpus foetidus

<400> SEQUENCE: 4

```
Met Gly Asp His Gly Pro Arg Thr Glu Ile Ser Phe Ala Gly Ser Ser
  1               5                  10                  15

Arg Ala Ala Phe Ala Ala Cys Phe Ala Glu Leu Cys Thr Ile Pro Leu
                 20                  25                  30

Asp Thr Ala Lys Val Arg Leu Gln Leu Gln Lys Lys Ala Val Thr Gly
             35                  40                  45

Asp Val Val Ala Leu Pro Lys Tyr Arg Gly Met Leu Gly Thr Val Ala
         50                  55                  60

Thr Ile Ala Arg Glu Glu Gly Leu Ser Ala Leu Trp Lys Gly Ile Val
 65                  70                  75                  80

Pro Gly Leu His Arg Gln Cys Leu Phe Gly Gly Leu Arg Ile Gly Leu
                 85                  90                  95

Tyr Glu Pro Val Lys Ser Phe Tyr Val Gly Asp Asn Phe Val Gly Asp
                100                 105                 110

Ile Pro Leu Ser Lys Lys Ile Leu Ala Gly Leu Thr Thr Gly Ala Leu
            115                 120                 125

Ala Ile Ile Val Ala Asn Pro Thr Asp Leu Val Lys Val Arg Leu Gln
        130                 135                 140

Ser Glu Gly Lys Leu Pro Pro Gly Val Pro Arg Arg Tyr Ser Gly Ala
145                 150                 155                 160

Leu Asn Ala Tyr Ser Thr Ile Val Lys Lys Glu Gly Leu Gly Ala Leu
                165                 170                 175

Trp Thr Gly Leu Gly Pro Asn Ile Ala Arg Asn Ala Ile Asn Ala
                180                 185                 190

Ala Glu Leu Ala Ser Tyr Asp Gln Val Lys Gln Met Lys Ser Arg Met
            195                 200                 205

Met Gly Asp Ser Ala Tyr Lys Ser Thr Phe Asp Cys Phe Ile Lys Thr
        210                 215                 220

Leu Lys Asn Asp Gly Pro Leu Ala Phe Tyr Lys Gly Phe Ile Pro Asn
225                 230                 235                 240

Phe Gly Arg Leu Gly Ser Trp Asn Val Ile Met Phe Leu Thr Leu Glu
                245                 250                 255
```

```
Gln Val Lys Lys Phe Phe Ile Lys Glu Val Pro Asn
        260                 265
```

<210> SEQ ID NO 5
<211> LENGTH: 306
<212> TYPE: PRT
<213> ORGANISM: Solanum Tuberosum

<400> SEQUENCE: 5

```
Met Gly Gly Gly Asp His Gly Gly Lys Ser Asp Ile Ser Phe Ala Gly
  1               5                  10                  15

Ile Phe Ala Ser Ser Ala Phe Ala Ala Cys Phe Ala Glu Ala Cys Thr
                 20                  25                  30

Leu Pro Leu Asp Thr Ala Lys Val Arg Leu Gln Leu Gln Lys Lys Ala
             35                  40                  45

Val Glu Gly Asp Gly Leu Ala Leu Pro Lys Tyr Arg Gly Leu Leu Gly
         50                  55                  60

Thr Val Gly Thr Ile Ala Lys Glu Glu Gly Ile Ala Ser Leu Trp Lys
 65                  70                  75                  80

Gly Ile Val Pro Gly Leu His Arg Gln Cys Ile Tyr Gly Gly Leu Arg
                 85                  90                  95

Ile Gly Met Tyr Glu Pro Val Lys Asn Leu Tyr Val Gly Lys Asp His
            100                 105                 110

Val Gly Asp Val Pro Leu Ser Lys Lys Ile Leu Ala Ala Leu Thr Thr
        115                 120                 125

Gly Ala Leu Gly Ile Thr Ile Ala Asn Pro Thr Asp Leu Val Lys Val
    130                 135                 140

Arg Leu Gln Ala Glu Gly Lys Leu Pro Ala Gly Val Pro Arg Arg Tyr
145                 150                 155                 160

Ser Gly Ala Leu Asn Ala Tyr Ser Thr Ile Val Lys Gln Glu Gly Val
                165                 170                 175

Arg Ala Leu Trp Thr Gly Leu Gly Pro Asn Ile Gly Arg Asn Ala Ile
            180                 185                 190

Ile Asn Ala Ala Glu Leu Ala Ser Tyr Asp Gln Val Lys Glu Ala Val
        195                 200                 205

Leu Arg Ile Pro Gly Phe Thr Asp Asn Val Val Thr His Leu Ile Ala
    210                 215                 220

Gly Leu Gly Ala Gly Phe Phe Ala Val Cys Ile Gly Ser Pro Val Asp
225                 230                 235                 240

Val Val Lys Ser Arg Met Met Gly Asp Ser Ala Tyr Lys Asn Thr Leu
                245                 250                 255

Asp Cys Phe Val Lys Thr Leu Lys Asn Asp Gly Pro Leu Ala Phe Tyr
            260                 265                 270

Lys Gly Phe Ile Pro Asn Phe Gly Arg Leu Gly Ser Trp Asn Val Ile
        275                 280                 285

Met Phe Leu Thr Leu Glu Gln Ala Lys Lys Phe Val Lys Ser Leu Glu
    290                 295                 300

Ser Pro
305
```

<210> SEQ ID NO 6
<211> LENGTH: 316
<212> TYPE: PRT
<213> ORGANISM: Arabidopsis thaliana

<400> SEQUENCE: 6

```
Met Val Ala Ala Gly Lys Ser Asp Leu Ser Leu Pro Lys Thr Phe Ala
 1               5                  10                  15

Cys Ser Ala Phe Ala Ala Cys Val Gly Glu Val Cys Thr Ile Pro Leu
                20                  25                  30

Asp Thr Ala Lys Val Arg Leu Gln Leu Gln Lys Ser Ala Phe Thr Leu
            35                  40                  45

Ala Gly Asp Val Thr Leu Pro Lys Tyr Arg Gly Leu Leu Gly Thr Val
        50                  55                  60

Gly Thr Ile Ala Arg Glu Gly Leu Arg Ser Leu Trp Lys Gly Val
65                  70                  75                  80

Val Pro Gly Leu His Arg Gln Cys Leu Phe Gly Gly Leu Arg Ile Gly
                85                  90                  95

Met Tyr Glu Pro Val Lys Asn Leu Tyr Val Phe Thr Gly Lys Asp Phe
                100                 105                 110

Val Gly Asp Val Pro Leu Ser Lys Lys Ile Leu Ala Gly Leu Thr Thr
            115                 120                 125

Gly Ala Leu Gly Ile Met Val Ala Asn Pro Thr Asp Leu Val Lys Val
        130                 135                 140

Arg Leu Gln Ala Glu Gly Lys Leu Ala Ala Gly Ala Pro Arg Arg Tyr
145                 150                 155                 160

Ser Gly Ala Leu Asn Ala Tyr Phe Thr Ser Thr Ile Val Arg Gln Glu
                165                 170                 175

Gly Val Arg Ala Leu Trp Thr Val Leu Gly Pro Asn Val Ala Arg Asn
            180                 185                 190

Ala Ile Ile Asn Ala Ala Glu Leu Ala Ser Tyr Asp Gln Val Lys Glu
        195                 200                 205

Thr Ile Leu Lys Ile Pro Gly Phe Thr Asp Asn Val Val Thr His Ile
210                 215                 220

Leu Ser Gly Leu Phe Thr Gly Ala Gly Phe Phe Ala Val Cys Ile Gly
225                 230                 235                 240

Ser Pro Val Asp Val Val Lys Ser Arg Met Met Gly Asp Ser Gly Ala
                245                 250                 255

Tyr Lys Gly Thr Ile Asp Cys Phe Val Lys Thr Leu Lys Ser Asp Gly
            260                 265                 270

Pro Met Ala Phe Tyr Lys Gly Phe Ile Pro Asn Phe Gly Arg Leu Gly
        275                 280                 285

Ser Phe Thr Trp Asn Val Ile Met Phe Leu Thr Leu Glu Gln Ala Lys
    290                 295                 300

Lys Tyr Val Arg Glu Leu Asp Ala Ser Lys Arg Asn
305                 310                 315

<210> SEQ ID NO 7
<211> LENGTH: 307
<212> TYPE: PRT
<213> ORGANISM: Homo sapiens

<400> SEQUENCE: 7

Met Gly Gly Leu Thr Ala Ser Asp Val His Pro Thr Leu Gly Val Gln
 1               5                  10                  15

Leu Phe Ser Ala Pro Ile Ala Ala Cys Leu Ala Asp Val Ile Thr Phe
                20                  25                  30

Pro Leu Asp Thr Ala Lys Val Arg Leu Gln Val Gln Gly Glu Cys Pro
            35                  40                  45

Thr Ser Ser Val Ile Arg Tyr Lys Gly Val Leu Gly Thr Ile Thr Ala
```

```
                50                  55                  60
Val Val Lys Thr Glu Gly Arg Met Lys Leu Tyr Ser Gly Leu Pro Ala
 65                  70                  75                  80

Gly Leu Gln Arg Gln Ile Ser Ser Ala Ser Leu Arg Ile Gly Leu Tyr
                 85                  90                  95

Asp Thr Val Gln Glu Phe Leu Thr Ala Gly Lys Glu Thr Ala Pro Ser
                100                 105                 110

Leu Gly Ser Lys Ile Leu Ala Gly Leu Thr Thr Gly Gly Val Ala Val
                115                 120                 125

Phe Ile Gly Gln Pro Thr Glu Val Val Lys Val Arg Leu Gln Ala Gln
130                 135                 140

Ser His Leu His Gly Ile Lys Pro Arg Tyr Thr Gly Thr Tyr Asn Ala
145                 150                 155                 160

Tyr Arg Ile Ile Ala Thr Thr Glu Gly Leu Thr Gly Leu Trp Lys Gly
                165                 170                 175

Thr Thr Pro Asn Leu Met Arg Ser Val Ile Ile Asn Cys Thr Glu Leu
                180                 185                 190

Val Thr Tyr Asp Leu Met Lys Glu Ala Phe Val Lys Asn Asn Ile Leu
                195                 200                 205

Ala Asp Asp Val Pro Cys His Leu Val Ser Ala Leu Ile Ala Gly Phe
210                 215                 220

Cys Ala Thr Ala Met Ser Ser Pro Val Asp Val Val Lys Thr Arg His
225                 230                 235                 240

Ile Asn Ser Pro Pro Gly Gln Tyr Lys Ser Val Pro Asn Cys Ala Met
                245                 250                 255

Lys Val Phe Thr Asn Glu Gly Pro Thr Ala Phe Phe Lys Gly Leu Val
                260                 265                 270

Pro Ser Phe Leu Arg Leu Gly Ser Trp Asn Val Ile Met Phe Val Cys
                275                 280                 285

Phe Glu Gln Leu Lys Arg Glu Leu Ser Lys Ser Arg Gln Thr Met Asp
                290                 295                 300

Cys Ala Thr
305

<210> SEQ ID NO 8
<211> LENGTH: 309
<212> TYPE: PRT
<213> ORGANISM: Homo sapiens

<400> SEQUENCE: 8

Met Val Gly Phe Lys Ala Thr Asp Val Pro Pro Thr Ala Thr Val Lys
  1               5                  10                  15

Phe Leu Gly Ala Gly Thr Ala Ala Cys Ile Ala Asp Leu Ile Thr Phe
                 20                  25                  30

Pro Leu Asp Thr Ala Lys Val Arg Leu Gln Ile Gln Gly Glu Ser Gln
             35                  40                  45

Gly Pro Val Arg Ala Thr Ala Ser Ala Gln Tyr Arg Gly Val Met Gly
         50                  55                  60

Thr Ile Leu Thr Met Val Arg Thr Glu Gly Pro Arg Ser Leu Tyr Asn
 65                  70                  75                  80

Gly Leu Val Ala Gly Leu Gln Arg Gln Met Ser Phe Ala Ser Val Arg
                 85                  90                  95

Ile Gly Leu Tyr Asp Ser Val Lys Gln Phe Tyr Thr Lys Gly Ser Glu
                100                 105                 110
```

-continued

```
His Ala Ser Ile Gly Ser Arg Leu Leu Ala Gly Ser Thr Thr Gly Ala
            115                 120                 125

Leu Ala Val Ala Val Ala Gln Pro Thr Asp Val Val Lys Val Arg Phe
130                 135                 140

Gln Ala Gln Ala Arg Ala Gly Gly Arg Arg Tyr Gln Ser Thr Val
145                 150                 155                 160

Asn Ala Tyr Lys Thr Ile Ala Arg Glu Glu Gly Phe Arg Gly Leu Trp
                165                 170                 175

Lys Gly Thr Ser Pro Asn Val Ala Arg Asn Ala Ile Val Asn Cys Ala
                180                 185                 190

Glu Leu Val Thr Tyr Asp Leu Ile Lys Asp Ala Leu Leu Lys Ala Asn
                195                 200                 205

Leu Met Thr Asp Asp Leu Pro Cys His Phe Thr Ser Ala Phe Gly Ala
210                 215                 220

Gly Phe Cys Thr Thr Val Ile Ala Ser Pro Val Asp Val Val Lys Thr
225                 230                 235                 240

Arg His Met Asn Ser Ala Leu Gly Gln Tyr Ser Ser Ala Gly His Cys
                245                 250                 255

Ala Leu Thr Met Leu Gln Lys Glu Gly Pro Arg Ala Phe Tyr Lys Gly
                260                 265                 270

Phe Met Pro Ser Phe Leu Arg Leu Gly Ser Trp Asn Val Val Met Phe
                275                 280                 285

Val Thr Tyr Glu Gln Leu Lys Arg Ala Leu Met Ala Ala Cys Thr Ser
                290                 295                 300

Arg Glu Ala Pro Phe
305
```

<210> SEQ ID NO 9
<211> LENGTH: 312
<212> TYPE: PRT
<213> ORGANISM: Homo sapiens

<400> SEQUENCE: 9

```
Met Val Gly Leu Lys Pro Ser Asp Val Pro Thr Met Ala Val Lys
  1               5                  10                  15

Phe Leu Gly Ala Gly Thr Ala Ala Cys Phe Ala Asp Leu Val Thr Phe
                 20                  25                  30

Pro Leu Asp Thr Ala Lys Val Arg Leu Gln Ile Gln Gly Glu Asn Gln
                 35                  40                  45

Ala Val Gln Thr Ala Arg Leu Val Gln Tyr Arg Gly Val Leu Gly Thr
 50                  55                  60

Ile Leu Thr Met Val Arg Thr Glu Gly Pro Cys Ser Pro Tyr Asn Gly
 65                  70                  75                  80

Leu Val Ala Gly Leu Gln Arg Gln Met Ser Phe Ala Ser Ile Arg Ile
                 85                  90                  95

Gly Leu Tyr Asp Ser Val Lys Gln Val Tyr Thr Pro Lys Gly Ala Asp
                100                 105                 110

Asn Ser Ser Leu Thr Thr Arg Ile Leu Ala Gly Cys Thr Thr Gly Ala
                115                 120                 125

Met Ala Val Thr Cys Ala Gln Pro Thr Asp Val Val Lys Val Arg Phe
                130                 135                 140

Gln Ala Ser Ile His Leu Gly Pro Ser Arg Ser Asp Arg Lys Tyr Ser
145                 150                 155                 160

Gly Thr Met Asp Ala Tyr Arg Thr Ile Ala Arg Glu Glu Gly Val Arg
                165                 170                 175
```

```
Gly Leu Trp Lys Gly Thr Leu Pro Asn Ile Met Arg Asn Ala Ile Val
            180                 185                 190

Asn Cys Ala Glu Val Val Thr Tyr Asp Ile Leu Lys Glu Lys Leu Leu
            195                 200                 205

Asp Tyr His Leu Leu Thr Asp Asn Phe Pro Cys His Phe Val Ser Ala
            210                 215                 220

Phe Gly Ala Gly Phe Cys Ala Thr Val Val Ala Ser Pro Val Asp Val
225                 230                 235                 240

Val Lys Thr Arg His Met Asn Ser Pro Pro Gly Gln Tyr Phe Ser Pro
            245                 250                 255

Leu Asp Cys Met Ile Lys Met Val Ala Gln Glu Gly Pro Thr Ala Phe
            260                 265                 270

Tyr Lys Gly Phe Thr Pro Ser Phe Leu Arg Leu Gly Ser Trp Asn Val
            275                 280                 285

Val Met Phe Val Thr Tyr Glu Gln Leu Lys Arg Ala Leu Met Lys Val
            290                 295                 300

Gln Met Leu Arg Glu Ser Pro Phe
305                 310

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: DNA Primer

<400> SEQUENCE: 10
tttttttttt tttttttttt tttt                                       24

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Conserved
      UCP Peptide Fragment

<400> SEQUENCE: 11

Cys Cys Ile Tyr Thr Ile Gly Ala Tyr Ala Cys Ile Gly Cys Ile Ala
  1               5                  10                  15

Ala Arg

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Conserved
      UCP Peptide Fragment

<400> SEQUENCE: 12

Ala Cys Trp Thr Thr Cys Cys Ala Ile Ser Tyr Ile Cys Cys Ile Ala
  1               5                  10                  15

Trp Ile Cys
```